United States Patent [19]

Casal Alvarez et al.

[11] Patent Number: 5,785,974
[45] Date of Patent: Jul. 28, 1998

[54] SYNTHETIC PEPTIDES AND VACCINES AGAINST PARVOVIRUS

[75] Inventors: José Ignacio Casal Alvarez; Carmen Vela Olmo. both of Madrid, Spain; Joannes Pieter Maria Langeveld. Harderwijk; Robert Hans Meloen. Lelystad, both of Netherlands; Kristian Dalsgaard. Kalvehave, Denmark

[73] Assignee: Immunologia Y Genetica Aplicada, S.A.. Madrid, Spain

[21] Appl. No.: 307,724

[22] PCT Filed: Jan. 21, 1994

[86] PCT No.: PCT/ES94/00006

§ 371 Date: Nov. 9, 1994

§ 102(e) Date: Nov. 9, 1994

[87] PCT Pub. No.: WO94/17098

PCT Pub. Date: Aug. 4, 1994

[30] Foreign Application Priority Data

Jan. 23, 1993 [ES] Spain ........................... 9300117
Jan. 20, 1994 [ES] Spain ........................... 9400111

[51] Int. Cl.[6] .................... A61K 39/23; A61K 39/235
[52] U.S. Cl. ............................ 424/233.1; 424/185.1; 424/186.1
[58] Field of Search ..................... 424/185.1, 186.1, 424/193.1, 199.1, 200.1, 233.1; 435/69.7, 172.1, 252.3; 530/300, 350

[56] References Cited

U.S. PATENT DOCUMENTS 5,498,413  3/1996  Casal Alvarez ................ 424/233.1

FOREIGN PATENT DOCUMENTS 0117063      1/1984   European Pat. Off. .
0117767 A    9/1984   European Pat. Off. .
WO 84/02847  2/1984   WIPO .
WO 91 12269  8/1991   WIPO .
WO 92/17205  1/1992   WIPO .
WO 93/01284  1/1993   WIPO .

OTHER PUBLICATIONS

Casal et al Journal of Virology Nov. 1995 pp. 7274–7277 vol. 69 No. 11, Nov. 1994.
Langeveld et al Vaccine vol. 13 No. 11:1033–1037 1995.
Langeveld et al Journal of Virology vol. 68 No. 7:4506–4513, Jul. 1994.
Rimmelzwaan et al Journal General Virology vol. 71:2741–2745, 1990.
Lopez de Turiso et al, Journal of General Virology, vol. 72, No. 10, 1991 pp. 2445–2456.
Langeveld et al Journal of Virology, vol. 67, No. 2, 1993, pp. 765–772.

Primary Examiner—Lila Feisee
Assistant Examiner—Julie E. Reeves
Attorney, Agent, or Firm—Harrison & Egbert

[57] ABSTRACT

An immunogenic peptide for use in the prevention of parvovirus infections having a contiguous sequence of 6 to 25 amino acids. The peptide is produced from autonomous parvoviruses so as to be capable of inducing neutralizing antibodies against such viruses. These peptides correspond to antigenic sites located in the first 25 amino acids of the amino terminal end of the VP2 proteins of parvoviruses. When these peptides are coupled to carrier proteins or to other immunogenic complexes, they can be used in the formulation of vaccines appropriate to protect dogs, cats, pigs and minks against the infections caused by the parvoviruses.

12 Claims, 4 Drawing Sheets

5,785,974

SEQUENCE LISTING ( 1 ) GENERAL INFORMATION:

( i i i ) NUMBER OF SEQUENCES: 40

( 2 ) INFORMATION FOR SEQ ID NO:1:

( i ) SEQUENCE CHARACTERISTICS:
        ( A ) LENGTH: 25 amino acids
        ( B ) TYPE: amino acids
        ( D ) TOPOLOGY: linear ( i i ) MOLECULE TYPE: Peptide ( v ) FRAGMENT TYPE: N-terminal end ( v i ) ORIGINAL SOURCE:
        ( A ) ORGANISM: Canine Parvovirus (CPV)
        ( B ) STRAIN: Type 2

( x i ) SEQUENCE DESCRIPTION: SEQ ID. NO: 1:

```
Met Ser Asp Gly Ala Val Gln Pro Asp Gly Gly Gln Pro Ala Val Arg
 1               5                  10                  15
Asn Glu Arg Ala Thr Gly Ser Gly Asn
                20                  25
```

( 2 ) INFORMATION FOR SEQ ID NO:2:

( i ) SEQUENCE CHARACTERISTICS:
        ( A ) LENGTH: 25 amino acids
        ( B ) TYPE: amino acids
        ( D ) TOPOLOGY: linear ( i i ) MOLECULE TYPE: Peptide ( v ) FRAGMENT TYPE: N-terminal end ( v i ) ORIGINAL SOURCE:
        ( A ) ORGANISM: Porcine Parvovirus (PPV)
        ( B ) STRAIN: NADL-2

( x i ) SEQUENCE DESCRIPTION: SEQ ID. NO: 2:

```
Met Ser Glu Asn Val Glu Gln His Asn Pro Ile Asn Ala Gly Thr Glu
 1               5                  10                  15
Leu Ser Ala Thr Gly Asn Glu Ser Gly
                20                  25
```

( 2 ) INFORMATION FOR SEQ ID NO:3:

( i ) SEQUENCE CHARACTERISTICS:
        ( A ) LENGTH: 16 amino acids
        ( B ) TYPE: amino acids
        ( D ) TOPOLOGY: linear ( i i ) MOLECULE TYPE: Peptide ( v ) FRAGMENT TYPE: N-terminal end ( v i ) ORIGINAL SOURCE:
        ( A ) ORGANISM: Canine Parvovirus (CPV)
        ( B ) STRAIN: Type 2

( x i ) SEQUENCE DESCRIPTION: SEQ ID. NO: 3:

```
Cys  Gly  Gln  Val  Lys  Arg  Asp  Asn  Leu  Ala  Pro  Met  Ser  Asp  Gly  Ala
 1              5                        10                       15
```

( 2 ) INFORMATION FOR SEQ ID NO:4:

( i ) SEQUENCE CHARACTERISTICS:
        ( A ) LENGTH: 16 amino acids
        ( B ) TYPE: amino acids
        ( D ) TOPOLOGY: linear ( i i ) MOLECULE TYPE: Peptide ( v ) FRAGMENT TYPE: N-terminal end ( v i ) ORIGINAL SOURCE:
        ( A ) ORGANISM: Canine Parvovirus (CPV)
        ( B ) STRAIN: Type 2

( x i ) SEQUENCE DESCRIPTION: SEQ ID. NO: 4:

```
Cys  Asp  Asn  Leu  Ala  Pro  Met  Ser  Asp  Gly  Ala  Val  Gln  Pro  Asp  Gly
 1              5                        10                       15
```

( 2 ) INFORMATION FOR SEQ ID NO:5:

( i ) SEQUENCE CHARACTERISTICS:
        ( A ) LENGTH: 16 amino acids
        ( B ) TYPE: amino acids
        ( D ) TOPOLOGY: linear ( i i ) MOLECULE TYPE: Peptide ( v ) FRAGMENT TYPE: N-terminal end ( v i ) ORIGINAL SOURCE:
        ( A ) ORGANISM: Canine Parvovirus (CPV)
        ( B ) STRAIN: Type 2

( x i ) SEQUENCE DESCRIPTION: SEQ ID. NO: 5:

```
Cys  Met  Ser  Asp  Gly  Ala  Val  Gln  Pro  Asp  Gly  Gly  Gln  Pro  Ala  Val
 1              5                        10                       15
```

( 2 ) INFORMATION FOR SEQ ID NO:6:

( i ) SEQUENCE CHARACTERISTICS:
        ( A ) LENGTH: 16 amino acids
        ( B ) TYPE: amino acids
        ( D ) TOPOLOGY: linear ( i i ) MOLECULE TYPE: Peptide ( v ) FRAGMENT TYPE: N-terminal end ( v i ) ORIGINAL SOURCE:
        ( A ) ORGANISM: Canine Parvovirus (CPV)
        ( B ) STRAIN: Type 2

( x i ) SEQUENCE DESCRIPTION: SEQ ID. NO: 6:

Cys Ser Asp Gly Ala Val Gln Pro Asp Gly Gln Pro Ala Val Arg
1               5                   10                  15

( 2 ) INFORMATION FOR SEQ ID NO:7:

( i ) SEQUENCE CHARACTERISTICS:
        ( A ) LENGTH: 16 amino acids
        ( B ) TYPE: amino acids
        ( D ) TOPOLOGY: linear ( i i ) MOLECULE TYPE: Peptide ( v ) FRAGMENT TYPE: N-terminal end ( v i ) ORIGINAL SOURCE:
        ( A ) ORGANISM: Canine Parvovirus (CPV)
        ( B ) STRAIN: Type 2

( x i ) SEQUENCE DESCRIPTION: SEQ ID. NO: 7:

Cys Asp Gly Ala Val Gln Pro Asp Gly Gln Pro Ala Val Arg Asn
1               5                   10                  15

( 2 ) INFORMATION FOR SEQ ID NO:8:

( i ) SEQUENCE CHARACTERISTICS:
        ( A ) LENGTH: 16 amino acids
        ( B ) TYPE: amino acids
        ( D ) TOPOLOGY: linear ( i i ) MOLECULE TYPE: Peptide ( v ) FRAGMENT TYPE: N-terminal end ( v i ) ORIGINAL SOURCE:
        ( A ) ORGANISM: Canine Parvovirus (CPV)
        ( B ) STRAIN: Type 2

( x i ) SEQUENCE DESCRIPTION: SEQ ID. NO: 8:

Cys Gly Ala Val Gln Pro Asp Gly Gly Gln Pro Ala Val Arg Asn Glu
1               5                   10                  15

( 2 ) INFORMATION FOR SEQ ID NO:9:

( i ) SEQUENCE CHARACTERISTICS:
        ( A ) LENGTH: 16 amino acids
        ( B ) TYPE: amino acids
        ( D ) TOPOLOGY: linear ( i i ) MOLECULE TYPE: Peptide ( v ) FRAGMENT TYPE: N-terminal end ( v i ) ORIGINAL SOURCE:
        ( A ) ORGANISM: Canine Parvovirus (CPV)
        ( B ) STRAIN: Type 2

( x i ) SEQUENCE DESCRIPTION: SEQ ID. NO: 9:

Cys Ala Val Gln Pro Asp Gly Gly Gln Pro Ala Val Arg Asn Glu Arg
1               5                   10                  15

( 2 ) INFORMATION FOR SEQ ID NO:10:

( i ) SEQUENCE CHARACTERISTICS:
        ( A ) LENGTH: 16 amino acids
        ( B ) TYPE: amino acids
        ( D ) TOPOLOGY: linear ( i i ) MOLECULE TYPE: Peptide ( v ) FRAGMENT TYPE: N-terminal end ( v i ) ORIGINAL SOURCE:
        ( A ) ORGANISM: Canine Parvovirus (CPV)

( B ) STRAIN: Type 2

( x i ) SEQUENCE DESCRIPTION: SEQ ID. NO: 10:

```
Cys Val Gln Pro Asp Gly Gly Gln Pro Ala Val Arg Asn Glu Arg Ala
1               5                   10                  15
```

( 2 ) INFORMATION FOR SEQ ID NO:11:

( i ) SEQUENCE CHARACTERISTICS:
        ( A ) LENGTH: 16 amino acids
        ( B ) TYPE: amino acids
        ( D ) TOPOLOGY: linear ( i i ) MOLECULE TYPE: Peptide ( v ) FRAGMENT TYPE: N-terminal end ( v i ) ORIGINAL SOURCE:
        ( A ) ORGANISM: Canine Parvovirus (CPV)
        ( B ) STRAIN: Type 2

( x i ) SEQUENCE DESCRIPTION: SEQ ID. NO: 11:

```
Cys Gln Pro Asp Gly Gly Gln Pro Ala Val Arg Asn Glu Arg Ala Thr
1               5                   10                  15
```

( 2 ) INFORMATION FOR SEQ ID NO:12:

( i ) SEQUENCE CHARACTERISTICS:
        ( A ) LENGTH: 16 amino acids
        ( B ) TYPE: amino acids
        ( D ) TOPOLOGY: linear ( i i ) MOLECULE TYPE: Peptide ( v ) FRAGMENT TYPE: N-terminal end ( v i ) ORIGINAL SOURCE:
        ( A ) ORGANISM: Canine Parvovirus (CPV)
        ( B ) STRAIN: Type 2

( x i ) SEQUENCE DESCRIPTION: SEQ ID. NO: 12:

```
Cys Pro Asp Gly Gly Gln Pro Ala Val Arg Asn Glu Arg Ala Thr Gly
1               5                   10                  15
```

( 2 ) INFORMATION FOR SEQ ID NO:13:

( i ) SEQUENCE CHARACTERISTICS:
        ( A ) LENGTH: 16 amino acids
        ( B ) TYPE: amino acids
        ( D ) TOPOLOGY: linear ( i i ) MOLECULE TYPE: Peptide ( v ) FRAGMENT TYPE: N-terminal end ( v i ) ORIGINAL SOURCE:
        ( A ) ORGANISM: Canine Parvovirus (CPV)
        ( B ) STRAIN: Type 2

( x i ) SEQUENCE DESCRIPTION: SEQ ID. NO: 13:

```
Cys Asp Gly Gly Gln Pro Ala Val Arg Asn Glu Arg Ala Thr Gly Ser
1               5                   10                  15
```

( 2 ) INFORMATION FOR SEQ ID NO:14:

( i ) SEQUENCE CHARACTERISTICS:
        ( A ) LENGTH: 16 amino acids
        ( B ) TYPE: amino acids
        ( D ) TOPOLOGY: linear ( i i ) MOLECULE TYPE: Peptide ( v ) FRAGMENT TYPE: N-terminal end ( v i ) ORIGINAL SOURCE:
            ( A ) ORGANISM: Canine Parvovirus (CPV)
            ( B ) STRAIN: Type 2

( x i ) SEQUENCE DESCRIPTION: SEQ ID. NO: 14:

Cys Gly Gln Pro Ala Val Arg Asn Glu Arg Ala Thr Gly Ser Gly Asn
1               5                   10                  15

( 2 ) INFORMATION FOR SEQ ID NO:15:

( i ) SEQUENCE CHARACTERISTICS:
              ( A ) LENGTH: 16 amino acids
              ( B ) TYPE: amino acids
              ( D ) TOPOLOGY: linear ( i i ) MOLECULE TYPE: Peptide ( v ) FRAGMENT TYPE: N-terminal end ( v i ) ORIGINAL SOURCE:
            ( A ) ORGANISM: Canine Parvovirus (CPV)
            ( B ) STRAIN: Type 2

( x i ) SEQUENCE DESCRIPTION: SEQ ID. NO: 15:

Cys Arg Asn Glu Arg Ala Thr Gly Ser Gly Asn Gly Ser Gly Gly Gly
1               5                   10                  15

( 2 ) INFORMATION FOR SEQ ID NO:16:

( i ) SEQUENCE CHARACTERISTICS:
              ( A ) LENGTH: 16 amino acids
              ( B ) TYPE: amino acids
              ( D ) TOPOLOGY: linear ( i i ) MOLECULE TYPE: Peptide ( v ) FRAGMENT TYPE: N-terminal end ( v i ) ORIGINAL SOURCE:
            ( A ) ORGANISM: Canine Parvovirus (CPV)
            ( B ) STRAIN: Type 2

( x i ) SEQUENCE DESCRIPTION: SEQ ID. NO: 16:

Cys Ala Val Asn Gly Asn Met Ala Leu Asp Asp Ile His Ala Gln Ile
1               5                   10                  15

( 2 ) INFORMATION FOR SEQ ID NO:17:

( i ) SEQUENCE CHARACTERISTICS:
              ( A ) LENGTH: 18 amino acids
              ( B ) TYPE: amino acids
              ( D ) TOPOLOGY: linear ( i i ) MOLECULE TYPE: Peptide ( v ) FRAGMENT TYPE: N-terminal end ( v i ) ORIGINAL SOURCE:
            ( A ) ORGANISM: Canine Parvovirus (CPV)
            ( B ) STRAIN: Type 2

( x i ) SEQUENCE DESCRIPTION: SEQ ID. NO: 17:

Cys Asn Val Val Leu Lys Thr Val Ser Glu Asp Ala Thr Gln Pro Pro
1               5                   10                  15

Thr Lys ( 2 ) INFORMATION FOR SEQ ID NO:18:

( i ) SEQUENCE CHARACTERISTICS:

(A) LENGTH: 16 amino acids
(B) TYPE: amino acids
(D) TOPOLOGY: linear (ii) MOLECULE TYPE: Peptide (v) FRAGMENT TYPE: N-terminal end (vi) ORIGINAL SOURCE:
(A) ORGANISM: Canine Parvovirus (CPV)
(B) STRAIN: Type 2

(xi) SEQUENCE DESCRIPTION: SEQ ID. NO: 18:

| Cys | Ser | Leu | Met | Val | Ala | Leu | Asp | Ser | Asn | Asn | Thr | Met | Pro | Phe | Thr |
|---|---|---|---|---|---|---|---|---|---|---|---|---|---|---|---|
| 1 | | | | 5 | | | | | 10 | | | | | 15 | |

(2) INFORMATION FOR SEQ ID NO:19:

(i) SEQUENCE CHARACTERISTICS:
(A) LENGTH: 16 amino acids
(B) TYPE: amino acids
(D) TOPOLOGY: linear (ii) MOLECULE TYPE: Peptide (v) FRAGMENT TYPE: N-terminal end (vi) ORIGINAL SOURCE:
(A) ORGANISM: Canine Parvovirus (CPV)
(B) STRAIN: Type 2

(xi) SEQUENCE DESCRIPTION: SEQ ID. NO: 19:

| Cys | Arg | Ala | Leu | Gly | Leu | Pro | Pro | Phe | Leu | Asn | Ser | Leu | Pro | Gln | Ser |
|---|---|---|---|---|---|---|---|---|---|---|---|---|---|---|---|
| 1 | | | | 5 | | | | | 10 | | | | | 15 | |

(2) INFORMATION FOR SEQ ID NO:20:

(i) SEQUENCE CHARACTERISTICS:
(A) LENGTH: 16 amino acids
(B) TYPE: amino acids
(D) TOPOLOGY: linear (ii) MOLECULE TYPE: Peptide (v) FRAGMENT TYPE: N-terminal end (vi) ORIGINAL SOURCE:
(A) ORGANISM: Canine Parvovirus (CPV)
(B) STRAIN: Type 2

(xi) SEQUENCE DESCRIPTION: SEQ ID. NO: 20:

| Cys | Gln | Ser | Glu | Gly | Ala | Thr | Asn | Phe | Gly | Asp | Ile | Gly | Val | Gln | Gln |
|---|---|---|---|---|---|---|---|---|---|---|---|---|---|---|---|
| 1 | | | | 5 | | | | | 10 | | | | | 15 | |

(2) INFORMATION FOR SEQ ID NO:21:

(i) SEQUENCE CHARACTERISTICS:
(A) LENGTH: 16 amino acids
(B) TYPE: amino acids
(D) TOPOLOGY: linear (ii) MOLECULE TYPE: Peptide (v) FRAGMENT TYPE: N-terminal end (vi) ORIGINAL SOURCE:
(A) ORGANISM: Canine Parvovirus (CPV)
(B) STRAIN: Type 2

(xi) SEQUENCE DESCRIPTION: SEQ ID. NO: 21:

| Cys | Leu | Phe | Val | Lys | Val | Ala | Pro | Asn | Leu | Thr | Asn | Glu | Tyr | Asp | Pro |
|---|---|---|---|---|---|---|---|---|---|---|---|---|---|---|---|
| 1 | | | | 5 | | | | | 10 | | | | | 15 | |

( 2 ) INFORMATION FOR SEQ ID NO:22:

( i ) SEQUENCE CHARACTERISTICS:
        ( A ) LENGTH: 16 amino acids
        ( B ) TYPE: amino acids
        ( D ) TOPOLOGY: linear ( i i ) MOLECULE TYPE: Peptide ( v ) FRAGMENT TYPE: N-terminal end ( v i ) ORIGINAL SOURCE:
        ( A ) ORGANISM: Canine Parvovirus (CPV)
        ( B ) STRAIN: Type 2

( x i ) SEQUENCE DESCRIPTION: SEQ ID. NO: 22:

Cys Gln Gln Met Ser Ile Asn Val Asp Asn Gln Phe Asn Tyr Val Pro
1               5                   10                  15

( 2 ) INFORMATION FOR SEQ ID NO:23:

( i ) SEQUENCE CHARACTERISTICS:
        ( A ) LENGTH: 16 amino acids
        ( B ) TYPE: amino acids
        ( D ) TOPOLOGY: linear ( i i ) MOLECULE TYPE: Peptide ( v ) FRAGMENT TYPE: N-terminal end ( v i ) ORIGINAL SOURCE:
        ( A ) ORGANISM: Canine Parvovirus (CPV)
        ( B ) STRAIN: Type 2

( x i ) SEQUENCE DESCRIPTION: SEQ ID. NO: 23:

Cys Lys Ile Val Tyr Glu Lys Ser Gln Leu Ala Pro Arg Lys Leu Tyr
1               5                   10                  15

( 2 ) INFORMATION FOR SEQ ID NO:24:

( i ) SEQUENCE CHARACTERISTICS:
        ( A ) LENGTH: 16 amino acids
        ( B ) TYPE: amino acids
        ( D ) TOPOLOGY: linear ( i i ) MOLECULE TYPE: Peptide ( v ) FRAGMENT TYPE: N-terminal end ( v i ) ORIGINAL SOURCE:
        ( A ) ORGANISM: Porcine Parvovirus (PPV)
        ( B ) STRAIN: NADL-2

( x i ) SEQUENCE DESCRIPTION: SEQ ID. NO: 24:

Cys Asn Thr Asn Ser Asn Ser Met Ser Glu Asn Val Glu Gln His Asn
1               5                   10                  15

( 2 ) INFORMATION FOR SEQ ID NO:25:

( i ) SEQUENCE CHARACTERISTICS:
        ( A ) LENGTH: 16 amino acids
        ( B ) TYPE: amino acids
        ( D ) TOPOLOGY: linear ( i i ) MOLECULE TYPE: Peptide ( v ) FRAGMENT TYPE: N-terminal end ( v i ) ORIGINAL SOURCE:
        ( A ) ORGANISM: Porcine Parvovirus (PPV)
        ( B ) STRAIN: NADL-2

( x i ) SEQUENCE DESCRIPTION: SEQ ID. NO: 25:

```
Cys  Met  Ser  Glu  Asn  Val  Glu  Gln  His  Asn  Pro  Ile  Asn  Ala  Gly  Thr
 1         5                        10                        15
```

( 2 ) INFORMATION FOR SEQ ID NO:26:

( i ) SEQUENCE CHARACTERISTICS:
        ( A ) LENGTH: 17 amino acids
        ( B ) TYPE: amino acids
        ( D ) TOPOLOGY: linear ( i i ) MOLECULE TYPE: Peptide ( v ) FRAGMENT TYPE: N-terminal end ( v i ) ORIGINAL SOURCE:
        ( A ) ORGANISM: Porcine Parvovirus (PPV)
        ( B ) STRAIN: NADL-2

( x i ) SEQUENCE DESCRIPTION: SEQ ID. NO: 26:

```
Cys  Val  Glu  Gln  His  Asn  Pro  Ile  Asn  Ala  Gly  Thr  Glu  Leu  Ser  Ala
 1         5                        10                        15
Thr
```

( 2 ) INFORMATION FOR SEQ ID NO:27:

( i ) SEQUENCE CHARACTERISTICS:
        ( A ) LENGTH: 16 amino acids
        ( B ) TYPE: amino acids
        ( D ) TOPOLOGY: linear ( i i ) MOLECULE TYPE: Peptide ( v ) FRAGMENT TYPE: N-terminal end ( v i ) ORIGINAL SOURCE:
        ( A ) ORGANISM: Porcine Parvovirus (PPV)
        ( B ) STRAIN: NADL-2

( x i ) SEQUENCE DESCRIPTION: SEQ ID. NO: 27:

```
Cys  Glu  Gln  His  Asn  Pro  Ile  Asn  Ala  Gly  Thr  Glu  Leu  Ser  Ala  Thr
 1         5                        10                        15
```

( 2 ) INFORMATION FOR SEQ ID NO:28:

( i ) SEQUENCE CHARACTERISTICS:
        ( A ) LENGTH: 16 amino acids
        ( B ) TYPE: amino acids
        ( D ) TOPOLOGY: linear ( i i ) MOLECULE TYPE: Peptide ( v ) FRAGMENT TYPE: N-terminal end ( v i ) ORIGINAL SOURCE:
        ( A ) ORGANISM: Porcine Parvovirus (PPV)
        ( B ) STRAIN: NADL-2

( x i ) SEQUENCE DESCRIPTION: SEQ ID. NO: 28:

```
Cys  Gln  His  Asn  Pro  Ile  Asn  Ala  Gly  Thr  Glu  Leu  Ser  Ala  Thr  Gly
 1         5                        10                        15
```

( 2 ) INFORMATION FOR SEQ ID NO:29:

( i ) SEQUENCE CHARACTERISTICS:
        ( A ) LENGTH: 16 amino acids
        ( B ) TYPE: amino acids
        ( D ) TOPOLOGY: linear ( i i ) MOLECULE TYPE: Peptide ( v ) FRAGMENT TYPE: N-terminal end (vi) ORIGINAL SOURCE:
    (A) ORGANISM: Porcine Parvovirus (PPV)
    (B) STRAIN: NADL-2

(xi) SEQUENCE DESCRIPTION: SEQ ID. NO: 29:

```
Cys His Asn Pro Ile Asn Ala Gly Thr Glu Leu Ser Ala Thr Gly Asn
 1               5                  10                  15
```

(2) INFORMATION FOR SEQ ID NO:30:

(i) SEQUENCE CHARACTERISTICS:
    (A) LENGTH: 17 amino acids
    (B) TYPE: amino acids
    (D) TOPOLOGY: linear (ii) MOLECULE TYPE: Peptide (v) FRAGMENT TYPE: N-terminal end (vi) ORIGINAL SOURCE:
    (A) ORGANISM: Porcine Parvovirus (PPV)
    (B) STRAIN: NADL-2

(xi) SEQUENCE DESCRIPTION: SEQ ID. NO: 30:

```
Cys Pro Ile Asn Ala Gly Thr Glu Leu Ser Ala Thr Gly Asn Glu Ser
 1               5                  10                  15
Gly
```

(2) INFORMATION FOR SEQ ID NO:31:

(i) SEQUENCE CHARACTERISTICS:
    (A) LENGTH: 16 amino acids
    (B) TYPE: amino acids
    (D) TOPOLOGY: linear (ii) MOLECULE TYPE: Peptide (v) FRAGMENT TYPE: N-terminal end (vi) ORIGINAL SOURCE:
    (A) ORGANISM: Porcine Parvovirus (PPV)
    (B) STRAIN: NADL-2

(xi) SEQUENCE DESCRIPTION: SEQ ID. NO: 31:

```
Cys Ala Gly Thr Glu Leu Ser Ala Thr Gly Asn Glu Ser Gly Gly Gly
 1               5                  10                  15
```

(2) INFORMATION FOR SEQ ID NO:32:

(i) SEQUENCE CHARACTERISTICS:
    (A) LENGTH: 17 amino acids
    (B) TYPE: amino acids
    (D) TOPOLOGY: linear (ii) MOLECULE TYPE: Peptide (v) FRAGMENT TYPE: N-terminal end (vi) ORIGINAL SOURCE:
    (A) ORGANISM: Porcine Parvovirus (PPV)
    (B) STRAIN: NADL-2

(xi) SEQUENCE DESCRIPTION: SEQ ID. NO: 32:

```
Ile His Val Leu Asn Ser Glu Ser Gly Ser Ala Gly Gln Met Val Gln
 1               5                  10                  15
Asp
```

(2) INFORMATION FOR SEQ ID NO:33:

(i) SEQUENCE CHARACTERISTICS:
  (A) LENGTH: 16 amino acids
  (B) TYPE: amino acids
  (D) TOPOLOGY: linear (ii) MOLECULE TYPE: Peptide (v) FRAGMENT TYPE: N-terminal end (vi) ORIGINAL SOURCE:
  (A) ORGANISM: Porcine Parvovirus (PPV)
  (B) STRAIN: NADL-2

(xi) SEQUENCE DESCRIPTION:

```
Cys Tyr Asn Asp Asp Glu Pro Asn Gly Ala Ile Arg Phe Thr Met Gly
 1               5                   10                  15
```

( 2 ) INFORMATION FOR SEQ ID NO:37:

( i ) SEQUENCE CHARACTERISTICS:
        ( A ) LENGTH: 20 amino acids
        ( B ) TYPE: amino acids
        ( D ) TOPOLOGY: linear ( i i ) MOLECULE TYPE: Peptide ( v ) FRAGMENT TYPE: N-terminal end ( v i ) ORIGINAL SOURCE:
        ( A ) ORGANISM: Porcine Parvovirus (PPV)
        ( B ) STRAIN: NADL-2

( x i ) SEQUENCE DESCRIPTION: SEQ ID. NO: 37:

```
Cys Gln His Gly His Leu Thr Thr Ser Ser Gln Glu Leu Glu Arg Tyr
 1               5                   10                  15
Thr Phe Asn Pro
 20
```

( 2 ) INFORMATION FOR SEQ ID NO:38:

( i ) SEQUENCE CHARACTERISTICS:
        ( A ) LENGTH: 19 amino acids
        ( B ) TYPE: amino acids
        ( D ) TOPOLOGY: linear ( i i ) MOLECULE TYPE: Peptide ( v ) FRAGMENT TYPE: N-terminal end ( v i ) ORIGINAL SOURCE:
        ( A ) ORGANISM: Porcine Parvovirus (PPV)
        ( B ) STRAIN: NADL-2

( x i ) SEQUENCE DESCRIPTION: SEQ ID. NO: 38:

```
Gln Gln Phe Asn Gln Gln Ala Pro Leu Asn Leu Glu Asn Thr Asn Asn
 1               5                   10                  15
Gly Thr Leu
```

( 2 ) INFORMATION FOR SEQ ID NO:39:

( i ) SEQUENCE CHARACTERISTICS:
        ( A ) LENGTH: 19 amino acids
        ( B ) TYPE: amino acids
        ( D ) TOPOLOGY: linear ( i i ) MOLECULE TYPE: Peptide ( v ) FRAGMENT TYPE: N-terminal end ( v i ) ORIGINAL SOURCE:
        ( A ) ORGANISM: Porcine Parvovirus (PPV)
        ( B ) STRAIN: NADL-2

( x i ) SEQUENCE DESCRIPTION: SEQ ID. NO: 39:

```
Cys Leu Pro Ser Asp Pro Ile Gly Gly Lys Ser Asn Met His Phe Met
 1               5                   10                  15
Asn Thr Leu
```

( 2 ) INFORMATION FOR SEQ ID NO:40:

( i ) SEQUENCE CHARACTERISTICS:
        ( A ) LENGTH: 19 amino acids
        ( B ) TYPE: amino acids

```
    ( D ) TOPOLOGY: linear ( i i ) MOLECULE TYPE: Peptide ( v ) FRAGMENT TYPE: N-terminal end ( v i ) ORIGINAL SOURCE:
        ( A ) ORGANISM: Porcine Parvovirus (PPV)
        ( B ) STRAIN: NADL-2

( x i ) SEQUENCE DESCRIPTION: SEQ ID. NO: 40:

Thr Glu Pro Thr Thr Glu Gly Asp Gln His Pro Asn Ser Glu Ser Gly
 1               5                  10                  15
Ser Ala Gly
```

1

SYNTHETIC PEPTIDES AND VACCINES AGAINST PARVOVIRUS

This application is the national stage 371 filing of PCT/ES94/00006, filed Jan. 21, 1994, which claims priority to Spanish applications P 93/00117 filed Jan. 23, 1993 and P 94/00111 filed Jan. 20, 1994.

FIELD OF THE INVENTION

The present invention relates to chemically synthesized viral peptides related to the major antigen (VP2) of the autonomous parvovirus capsid and to assays and vaccines using the said peptides. The said peptides can, for instance, induce antibodies neutralizing for Canine Parvovirus (CPV), mink enteritis virus (MEV) and Porcine Parvovirus (PPV), whence they can be formulated in vaccines and respectively confer total protection against CPV, MEV and PPV in dogs, minks and pigs.

BACKGROUND OF THE INVENTION

Parvoviruses form a viral family having certain common features (Cotmore et al., Adv. Virus Res. 33:91–174 (1987)). They are the smallest known DNA viruses. Their genome is formed by a single stranded linear DNA molecule having a length of some 5.0 kb enclosed within a proteic capsid, being icosahedral in shape and having a size of approximately 25 nm. Two large open reading frames (ORF) are detected in the viral genome. The left ORF codes for non-structural proteins involved in viral replication whereas the right ORF codes for structural proteins forming the viral capsid, which is constituted by VP1, VP2 and VP3 proteins. The mRNA of both ORFs is polyadenylated and 3'-coterminal. There are approximately 60 copies of VP2 in the viral capsid and approximately 10 copies of VP1 (Wobble et al., Biochemistry 23, 6565–6569, 1984) which may be arranged as either homo- or heterodimers (Paradiso, J. Virol., 46, 94–102, 1983). The VP2 protein contains all the antigenic determinants involved in neutralizing the virus (López de Turiso et al., J. Gen. Virol., 72, 2445–2456 (1991); Langeveld et al., J. Virol., Vol. 67, No. 2, 765–772 (1993); López de Turiso et al., J. Virol., Vol. 66, No. 5, 2748–2753 (1991)).

Autonomous parvoviruses are responsible for a large number of diseases affecting human beings and animals of interest alike and may indeed be fatal because of the tendency of autonomous parvoviruses to replicate in proliferating cerebellum, lymphoid tissue, intestinal epithelium or foetal tissue cells. Among these autonomous parvoviruses are CPV, MEV, PPV, bovine parvovirus (BPV), goose parvovirus (GPV), feline panleukopenia virus (FPLV) and B19 parvovirus which affects human beings.

In this description the autonomous parvoviruses CPV and PPV will be focussed on as an example. Some of the main features of both parvoviruses are summarised hereinbelow.

Canine Parvovirus (CPV)

Within the genus of autonomous parvoviruses, CPV is a member of the feline parvovirus subgroup. The other members of this subgroup, very related each other, are feline panleukopenia virus (FPLV) and MEV. CPV causes severe enteritis in dogs of all ages and myocarditis in puppies less than 12 weeks old. CPV was first isolated in 1978 (Burtonboy, G. et al., Arch. Virol. 61:1–11 (1979); Appel et al., Vet. Rec. 105, 156–179, (1979)) and it is believed to have arisen as a natural variant of FPLV or MEV.

Protein and DNA sequence studies and serologic studies show a large antigenic and genetic homology between CPV, FPLV, MEV and the Raccoon Parvovirus (Tratschin et al., J. Gen Virol. 61:33–41 (1982); Carlsson et al., J. Virol., 55, 574–582 (1985); Parrish et al., Arch. Virol. 72, 267–278 (1982); Reed et al., J. Virol. 62:266–276 (1988)). Despite this homology they are exquisitely specific in the "in vivo" host, although "in vitro" all viruses replicate in cat kidney cells (Appel et al., Vet. Rec. 105, 156–179 (1979); Trastschin et al., J. Gen. Virol., 61:33–41, (1982)). The CPV capsid contains two proteins with broadly overlapping amino acid sequences, VP1 (82–84 KDa) and VP2 (67–70 KDa) (Paradiso et al., J. Gen. Virol. 39, 800–807, (1982); Surleraux et al., Arch Virol., 82, 233–240 (1984); J. Gen. Virol. 62, 113–125, (1982)). VP2 in full capsids (holding DNA) is preferentially broken down by proteolytic digestion into 63–67 KDa VP3 (Paradiso et al., Gen. Virol. 39, 800–807 (1982); Surleaux et al. Arch. Virol., 82, 233–240 (1984)) after capsid assembly (Paradiso, J. Virol., 39, 800–807 (1981)). The three-dimensional structure of the CPV capsid is currently known (Tsao et al., Science 251: 1456–1464 (1991)).

Our laboratory has investigated into the immunogenicity of various fragments of the proteins making up the CPV viral capsid, which has resulted in new VP2 protein and VP2 and VP1 peptides based recombinant vaccines being described. These findings are summarised in Spanish patents numbers P9002074, which relates to the expression of such products in *E. coli* bacterial systems; and P9100844, which relates to the expression of VP2 in a recombinant baculovirus system.

Ten antigenic sites in the VP2 sequence and their spatial location upon the capsid surface have been identified (J. Langeveld et al., J. Virol. 67, No. 2 (1993)).

Four potential neutralization sites have been described in CPV. Two such sites were mapped with synthetic peptides and of these, one is found at the N-terminal end and the other at positions 147–163 of VP2 (Rimmelzwaan et al., J. Gen. Virol., 71:2741–2745 (1990)). The two other sites were mapped on and about a large protuberant domain on the three-fold axis of symmetry of the viral capsid (Parrish et al., Virology 166:293–307 (1988)).

The role of the amino terminal end of VP2 in parvovirus is the subject of speculation. This domain is important because (a) "in vitro" viral neutralization has been observed when a monoclonal antibody specific to this site is used (López de Turiso et al., J. Gen. Virol., 72:2445–2456 (1991)), (b) it is immunogenic in various animal species (Langeveld et al., J. Virol., Vol. 67, No. 2, 765–772 (1993)) and (c) it is involved in the attachment of the virus to the cell.

The peptidic vaccines described herein are directed against part of this site. The knowledge of antigenic sites in VP2 led to a collection of synthetic peptides of potential interest in vaccine formulation being designed. Synthetic peptides including amino acids of the amino terminal end of VP2 consistently induced neutralizing antibodies in test animals. This domain is therefore an attractive candidate for its inclusion in a synthetic peptide vaccine.

Conventional CPV vaccines based upon live or inactivated virus and recombinant vaccines are currently available but there are no synthetic vaccines capable of inducing antibodies neutralizing CPV and effectively protecting dogs from CPV infection. These vaccines would provide manifold advantages, being not only economic but operative. Vaccines based on synthetic peptides are safe, because they eliminate the risks stemming from the handling and diffusion of the infectious agents inherent in conventional vaccines, are easy to produce, are highly reproducible and are very stable. In the case of CPV, another significant advantage of a synthetic vaccine is its potential to prevent vaccinal problems arising from the natural immunity in young puppies. Conventional CPV vaccines do not ensure complete protection in puppies less than 10 weeks old, for such have maternal antibodies which eliminate the vaccine. The data known heretofore point to the fact that among the general population of anti-virus antibodies in infected animals, anti-peptide antibodies are not present in large quantities, if at all. If antibodies induced by synthetic peptides are not predominant "in vivo" the peptidic vaccine would allow the immune response in the neonate at an earlier age than under current conditions.

Now therefore, an object of the present invention lies in new chemically synthesized peptides which include all or part of the terminal amino end of VP2 in CPV capable of inducing antibodies and neutralizing CPV.

Given the close homology (in excess of 98%) between CPV, MEV and FPLV it is very likely that an agent capable of inducing protection in dogs will have this same effect in other hosts, such as cats and minks. This effect will, for instance, be demonstrated in minks. Consequently, these new peptides may be used for obtaining immunogenic compositions and in formulating new synthetic vaccines capable of protecting dogs and, alternatively, minks and cats, respectively from CPV, MEV and FPLV infections. The said immunogenic compositions and vaccines are a further object of this invention.

Porcine Parvovirus (PPV)

PPV causes reproductive failures in pigs, leading to death and foetal mummification, abortions and other reproductive failures in pregnant pigs (Joo & Johnson, Veterinary Bulletin 46, 653–660 (1976); Mengeling, J. Am. Vet. Med. Assoc. 172, 1291-1294 (1978)). PPV contains a single-stranded DNA molecule with approximately 5000 nucleotides (Mollitor et al., Virology 137, 241-254 (1984)). The full sequence of the PPV genome has been described by our group (Ranz et al., J. Gen. Virol. 70, 2541-2553 (1989)). Four specific virus proteins have been described: three proteins forming the capsid (VP1, VP2 and VP3 with respective molecular weights of 83000, 64000 and 60000 dalton) and a non-structural protein NS1. Of the three structural proteins, the VP2 protein in PPV, just as VP2 in CPV, contains probably all the antigenic determinants involved in PPV neutralization.

There currently exist vaccines which provide porcine parvovirus protection based upon traditional inactivation methods with chemical agents and/or search of attenuated mutants for the virus. All previous attempts at producing new vaccines using recombinant proteins produced in prokaryotic microorganisms (v.gr. E. coli) have however failed.

In recent years, our laboratory has been working on PPV molecular biology (A. Ranz et al., J. Gen. Virol. 70, 2541-2553 (1989)); J. I. Casal et al., Virology, 177, 764-767 (1990)). These papers are related to the knowledge of viral DNA sequences which code for the proteins forming the PPV capsid. These sequences allowed us to identify the gene coding for VP2 in PPV and manipulate and insert the same in suitable vectors for expressing the same in a baculovirus system, as described in Spanish patent no. P9100845, related to the expression of VP2 in a recombinant baculovirus vector.

Using techniques resembling those used with CPV, assays were conducted designed to establish and search for antigenic sites in PPV. The results obtained showed that, as with CPV, the amino terminal end of VP2 in PPV is a potential neutralization site.

Therefore, although there are currently conventional and recombinant PPV vaccines available, there is no synthetic vaccine capable of effectively protecting pigs from PPV infection. It would be useful to have synthetic vaccines incorporating small peptides capable of inducing neutralizing antibodies, which would be both economically and operatively beneficial.

Consequently, a further object of this invention lies in new synthetic peptides stemming from the amino terminal end of VP2 in PPV, capable of inducing antibodies neutralizing PPV, which may be used in the production of immunogenic compositions and in formulating new synthetic vaccines capable of protecting pigs from PPV infection. These synthetic peptides are based upon the immunogenic properties of the amino end of VP2 the major protein in PPV. The immunogenic compositions and vaccines which incorporate such peptides are a further object of this invention.

Similarly, because of the structural similarity between the amino terminal ends of the VP2 proteins in all autonomous parvoviruses and the fact that in all animals tested in this invention (rabbits, hamsters, dogs, minks and pigs) consistently good titres of neutralizing antibodies were obtained, it follows that synthetic peptides found at similar positions, i.e. at the amino terminal end of the relevant VP2 proteins, could also be used to vaccinate humans against B19 Parvovirus, cattle against Bovine Parvovirus (BPV), geese against Goose Parvovirus (GPV) and, in general, against any other autonomous Parvovirus.

⊟: anti-1L15 titre in control dog (3025) serum

▲: anti-1L15 titre in immunized dog (3029) serum

⊖: anti-1L15 titre in immunized dog (3030) serum

■: anti-7L15 titre in sentry dog (3025) serum

▲: anti-7L15 titre in immunized dog (3029) serum

●: anti-7L15 titre in immunized dog (3030) serum

Figure 3:
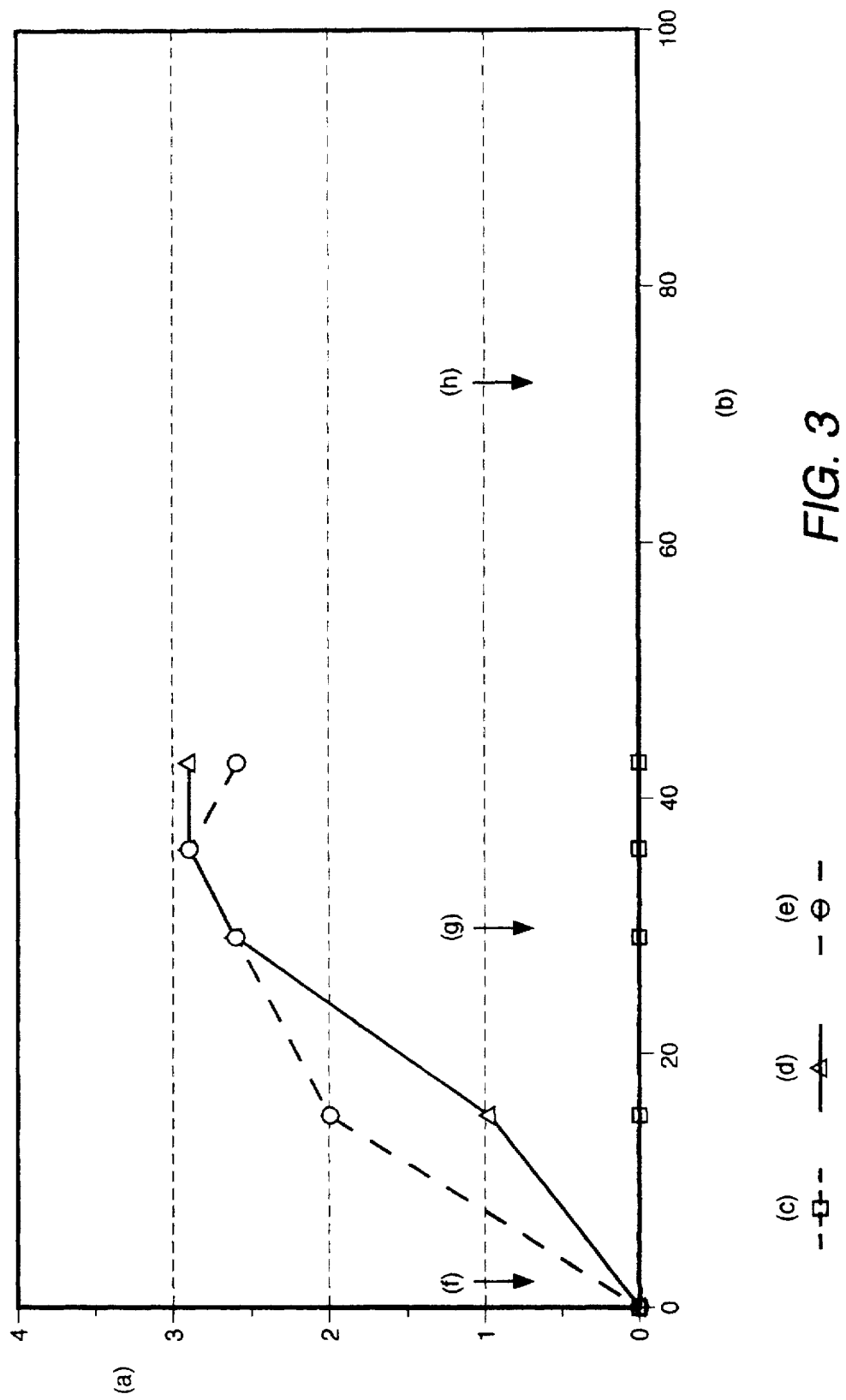

FIG. 3: shows the results obtained in establishing the titre of antibodies neutralizing CPV in the serum of control dog (3025 ⊟) and dogs immunized with peptides of this invention (3029 ▲ and 3030 ⊖).

Figure 4:
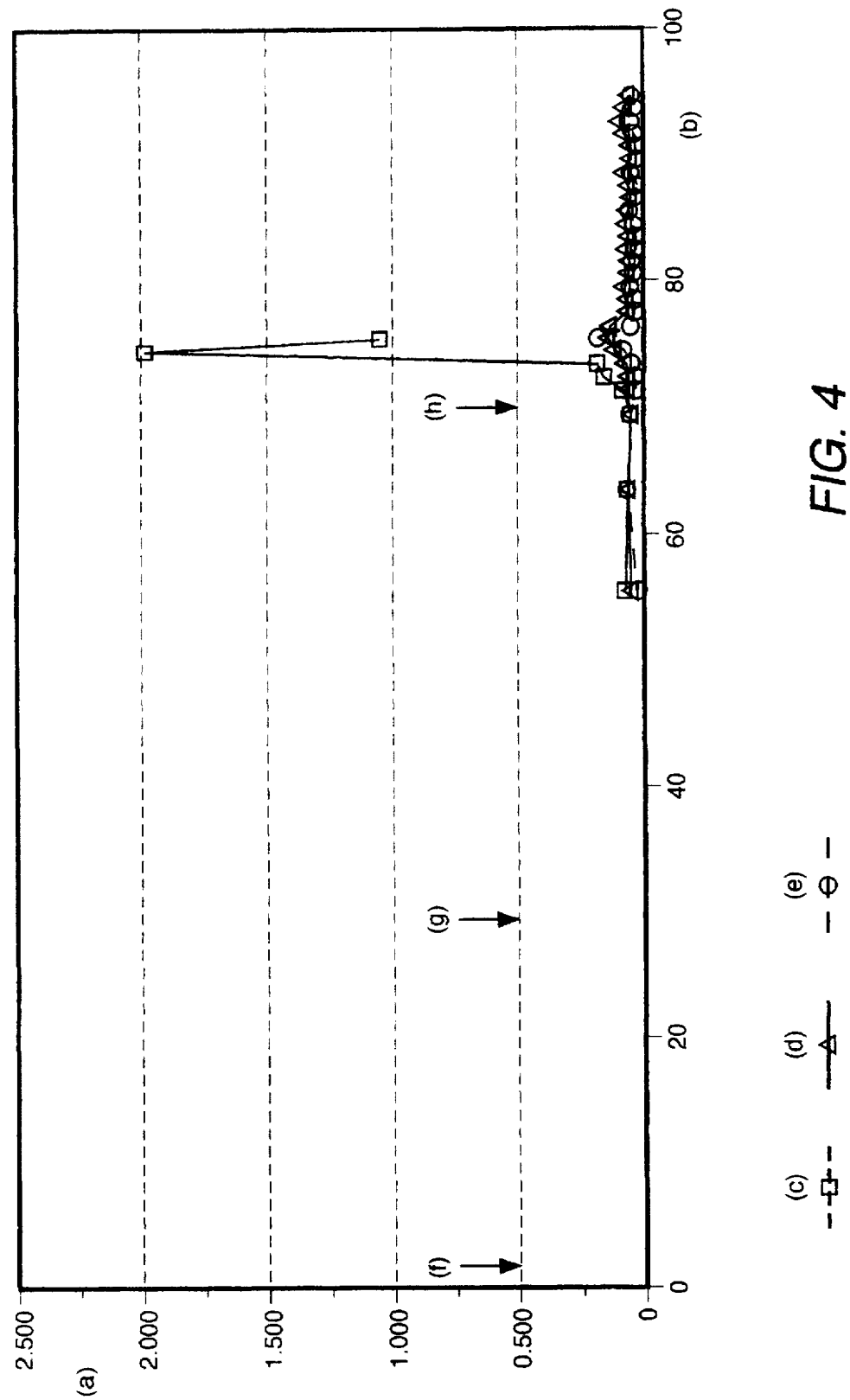

FIG. 4: shows the results obtained in establishing the presence of CPV in the faeces of immunized dogs (3029 ▲ and 3030 ⊖) and in the faeces of control dog (3025 ⊟) using a specific viral antigen ELISA.

DETAILED DESCRIPTION OF THE INVENTION

The invention provides new peptides useful in preparing suitable synthetic vaccines for protecting animals from infections caused by autonomous parvoviruses, such as CPV, MEV, FPLV and PPV. The new vaccines contain at least a chemically synthesized peptide originating in the amino terminal region of the VP2 protein in CPV or the VP2 protein in PPV. As used herein, terminal amino region should be construed as the region comprising at least the first twenty-five amino acids of the VP2 protein.

1. CPV

It has been found by PEPSCAN analysis (Geysen H. M. et al., Proc. Natl. Acad. Sci., USA, 81:3998–4002 (1984)) that there are ten antigenic sites in the VP2 of CPV (Langeveld et al., cited supra). Other authors have described other antigenic sites (Rimmelzwaan et al., and Parrish et al., (1988) cited supra). Based upon all the sites described a collection of peptides was synthesized to cover such sites. On investigating the immunogenicity of all the synthesized peptides it was found that only the peptides originating in the first twenty-five amino acids at the amino terminal end of the VP2 in CPV, coupled to KLH [Keyhole Limpet Hemocyanin] were capable of inducing neutralizing antisera in rabbits. The said peptides are capable of protecting dogs from the pathogenic effects of CPV infection.

The peptides capable of inducing antibodies neutralizing CPV, provided by this invention, are contained within Identified Sequence No. 1 (SEQ. ID. NO.: 1) [see the section regarding the Sequence List]. The attached Sequence Listing is incorporated by reference hereto.

This invention includes all the peptides comprised within SEQ. ID. NO.: 1 or resulting from the substitution of some of the amino acids shown in SEQ. ID. NO.: 1 with other functionally equivalent amino acids, or from the deletion or insertion of some such amino acids provided the resultant peptides are capable of inducing antibodies neutralizing CPV. Synthetic peptides with a length of between 6 and 20 amino acids are preferred for practical reasons.

Generally speaking, the peptides of the invention shall preferably be soluble in order that they may be coupled to suitable carrier proteins enhancing their immunogenic character, such as the KLH protein or any other protein used habitually in this field.

To obtain and select the synthetic peptides of this invention the following steps were basically taken:

a) Chemically synthesizing the peptides corresponding to the most immunogenic regions of the VP2 protein in CPV.

b) Coupling such peptides to a carrier protein.

c) Selecting the peptides inducing an antibody response in rabbits capable of neutralizing CPV.

d) Immunizing dogs with the peptides selected above and holding and carrying out a challenge test with virulent virus to check protection of dogs from infection.

These steps will be described hereinafter in greater detail. In a specific embodiment (Example 1) twenty-one pentadecapeptides were synthesized using Fmoc chemistry (Fields C. G. et al., Peptide Res., 4:95–101 (1991)) which briefly comprises:

(a) preparing a resin (solid phase) incorporating the amino acid of the C-terminal end with its amino end protected by a suitable protector group such as Fmoc (9-fluorophenyl-methyl-oxy-carbonyl) or the like (ter-butoxycarbonyl, benzyloxycarbonyl, p-toluenesulphonyl, triphenylmethyl, or o-nitrophenylsulphenyl);

(b) successively incorporating in a suitable order the remaining amino acids with their amino groups duly protected;

(c) leaving the synthesized peptide without protection and separating the same from the resin by suitable treatment; and (d) purifying the chemically synthesized peptide. The twenty-one synthesized peptides were coupled (Example 3), where possible, to the carrier KLH protein and used to immunize rabbits (Example 4). With immunization over it was found that the 1L15, 2L15, 3L15, 4L15, 5L15, 6L15, 7L15, 8L15 and 9L15 peptides were capable of inducing antibodies neutralizing CPV.

It was additionally found that dogs vaccinated with a mixture of the 1L15 and 7L15 peptides developed a high titre of antibodies neutralizing the virus and were protected from later infection with virulent virus (Example 5). Based upon these results it can be stated that the peptides provided by this invention can be used in formulating new synthetic vaccines in order to protect animals from CPV infection. Furthermore, due to the structural resemblance and the quasi-identity of the sequences of the first twenty-five amino acids of the terminal amino ends of the VP2 proteins in CPV, MEV and FPLV, it has been shown that peptides comprised within ID. SEQ. No. 1 are capable of inducing antibodies "in vivo" neutralizing MEV and can therefore be used in formulating vaccines capable of protecting minks from MEV infection. Indeed, it has been found that minks vaccinated with a mixture of the 1L15 and 7L15 peptides were protected from later infection with virulent virus (Example 6). It can be assumed from this test confirmation with MEV that the peptides included within SEQ. ID. NO.: 1 can induce FPLV protection in cats due to the structural homology between CPV, MEV and FPLV, which all belong to the same parvovirus subgroup.

Furthermore, given the structural homology there is between all the autonomous parvoviruses it was assumed that using the same procedure similar results could be found in other parvoviruses, such as PPV, BPV or the human B19 parvovirus. This demonstration was, for instance, made in PPV.

2. PPV

This invention also provides new peptides useful in the production of suitable synthetic vaccines for protecting pigs from PPV infection. These chemically synthesized peptides originate in the terminal amino region of the VP2 protein in PPV. The immunogenicity of the VP2 in PPV was first investigated using a strategy similar to that followed in the case of the VP2 in CPV. The sequence was analyzed by PEPSCAN and a collection of peptides located at the identified antigenic regions was synthesized. These peptides, coupled to KLH, were used to immunize rabbits and it was again found that only the peptides lying in the amino terminal region were capable of inducing antibodies neutralizing PPV and hence protecting pigs from the pathogenic effects of PPV infection. These synthetic peptides are included in SEQ. ID. NO.: 2.

This invention includes all peptides comprised within SEQ. ID. NO.: 2 or resulting from the substitution of some of the amino acids shown in SEQ. ID. NO.: 2 with other functionally equivalent amino acids or the deletion or insertion of some such amino acids, provided that the resultant peptides are capable of inducing antibodies neutralizing PPV. Synthetic peptides with a length of between 6 and 20 amino acids are preferred for practical reasons.

Generally speaking, the peptides of the invention shall preferably be soluble in order that they may be coupled to suitable carrier proteins enhancing their immunogenic character, such as the KLH protein.

To obtain and select the synthetic peptides of this invention the following steps were basically followed:

a) Chemically synthesizing the peptides corresponding to the most immunogenic regions of the VP2 protein in PPV.

b) Coupling such peptides to a carrier protein.

c) Selecting the peptides inducing an antibody response in rabbits capable of neutralizing PPV.

d) Immunizing pigs with the peptides selected above.

These steps will be described hereinafter in greater detail. In a specific embodiment (Example 2) seventeen solid phase peptides were synthesized using Fmoc chemistry, as mentioned before in relation to synthetic CPV peptides.

The seventeen peptides synthesized were coupled to the carrier KLH protein (Example 3) and were used to immunize rabbits (Example 7). With immunization over it was found that the peptides designated 1L15, 5L16, 6L15, 8L15, 10L16 and 13L16 were capable of inducing antibodies neutralizing PPV (Table 5). Based upon these results it can be stated that such peptides can be used in formulating new synthetic vaccines in order to protect animals from PPV infection.

3. Immunogenic compositions and vaccines

Immunogenic compositions can be prepared taking the peptides provided by this invention which contain the said peptides in immunogenic form, whence they can be used to formulate vaccines capable of protecting dogs, cats and minks respectively from CPV, FPLV and MEV infection (to which end peptides comprised within SEQ. ID. NO.: 1 will be used) and to formulate vaccines capable of protecting pigs from PPV infection (to which end peptides comprised within SEQ. ID. NO.: 2 will be used). The said immunogenic compositions can be prepared by coupling at least one of the peptides of this invention to a suitable carrier protein or multimeric structure. PCT Patent application published with number WO 90/11298 contains several references relating to coupling methods and carrier proteins which may be used. In a preferred embodiment of this invention compositions are provided which comprise an immunogenic conjugate of a protein (KLH) and a peptide of this invention. Alternatively, these compositions can contain an immunogenic complex obtained by crossing the peptide or an immunogenic recombinant protein containing one of the peptides of this invention.

This invention also provides vaccines that are characterized by comprising one of the aforesaid immunogenic compositions combined with at least an immunological adjuvant. Such vaccines can be prepared suspending at least one of the peptides of the invention coupled to a suitable carrier protein or multimeric structure, in an immunologically acceptable diluent plus an adjuvant. Additionally, a vaccine can contain a mixture of the peptides of this invention as immunogenic agents. Acceptable immunological diluents used are saline solutions with phosphate, tris or other like saline solutions. The adjuvant used can be alumina gel suspensions alone or combined with other adjuvants used habitually in the formulation of vaccines such as QuilA or the like having a similar power.

DETAILED DESCRIPTION OF AN EMBODIMENT OF THE INVENTION (EXAMPLES)

Example 1

CHEMICAL SYNTHESIS OF CPV PEPTIDES AND SELECTION OF IMMUNOGENIC PEPTIDES

Based upon the data as to the location of B epitopes on the CPV capsid (Langeveld et al., cited supra) the twenty-one peptides shown in Table 1 were synthesized.

TABLE 1[1]

| PEPTIDE CODE | SEQUENCE SEQ ID NO |
| --- | --- |
| -10L15 | *GQVKRDNLAPMSDGA#3 |
| -5L15 | *DNLAPMSDGAVQPDG#4 |
| 1L15 | *MSDGAVQPDGGQPAV#5 |
| 2L15 | *SDGAVQPDGGQPAVR#6 |
| 3L15 | *DGAVQPDGGQPAVRN#7 |
| 4L15 | *GAVQPDGGQPAVRNE#8 |
| 5L15 | *AVQPDGGQPAVRNER#9 |
| 6L15 | *VQPDGGQPAVRNERA#10 |
| 7L15 | *QPDGGQPAVRNERAT#11 |
| 8L15 | *PDGGQPAVRNERATG#12 |
| 9L15 | *DGGQPAVRNERATGS#13 |
| 11L15 | *GQPAVRNERATGsGN#14 |
| 16L15 | *RNERATGSGNGSGGG#15 |
| 91L15 | *AVNGNMALDDIHAQI#16 |
| 147L17 | *NVVLKTVSEDATQPPTK#17 |
| 172L15 | *SLMVALDSNNTMPFT#18 |
| 283L15 | *RALGLPPFLNSLPQS#19 |
| 296L15 | *QSEGATNFGDIGVQQ#20 |
| 498L15 | *LFVKVAPNLTNEYDP#21 |
| 549L15 | *QQMSINVDNQFNYVP#22 |
| 570L15 | *KIVYEKSQLAPRKLY#23 |

[1]In both Table 1 and Table 2:
-each letter in the sequence stands for an amino acid designated pursuant to the single letter amino acid nomenclature code (Structural Biochemistry, P. Louisot, Ed. AC, 1st. Edition (1977), pages 372–373);
-the amino terminal end is located to the left of the sequence whereas the carboxy terminal end is located to the right of the sequence;
-the peptide code shows the position of the residue of the N-terminal end in the VP2 sequence (before L) and the length (L) of the peptide, stated as a number of amino acid residues (behind L);
*: stands for a Cysteine residue with the acetylated amino group; and
: denotes that the carboxy group of the carboxy terminal amino acid residue is amidated.

Save for the 157L17 heptadecapeptide, the length of the peptides was of 15 amino acid residues, not including the N-terminal cysteine which was used for coupling. Sixteen peptides were sufficiently soluble to allow their conjugation to KLH whereas the other six displayed only a limited solubility (less than 10%). The synthesis of these peptides was carried out using Fmoc chemistry (Saxon Biochemical, Germany), pursuant to the general process mentioned above, on Rink™ resins (Saxon). RINK™ is an amide resin, namely, a 4-(2',4'-dimethoxyphenyl—FMOC—aminomethyl)phenoxy resin. RINK™ is manufactured and sold by Saxon Biochemical of Germany. Synthesis was carried out either manually in glass vessels or in an Applied Biosystems 430A synthesizer. The sequences are acetylated at the N-terminal end and amidated at the C-terminal.

The peptides were purified using high performance liquid chromatography (HPLC). Quality was analyzed in a Delta PaK 5μ C18-100A (0.39×15 cm) column, with a 680 gradient controller and a 991 diode array detector. An acetonitrile gradient of 0 to 80% (1%/min) in water, and 0.1% trifluoroacetic acid (TFA) at 30° C. and a flow of 1 ml/min were used. Before being coupled to KLH, the peptides were purified on a 2×25 cm C18 Bischoff Prap 2025 column in Hewlett Packard 1082B HPLC equipment and with a reading at 225 nm. Methanol gradients with a methanol increase of 1% per min at a flow of 10 ml/min in water and 0.1% (v/v) of trifluoroacetic acid (TFA) were used. Depending on the peptide, the initial methanol concentrations varied between 0 and 20%. The amino acid composition analysis was carried out in accordance with the Pico-tag (Waters) processes.

Example 2

CHEMICAL SYNTHESIS OF PPV PEPTIDES AND SELECTION OF IMMUNOGENIC PEPTIDES

Based upon the data as to the location of B epitopes on the PPV capsid, the seventeen peptides shown in Table 2 were synthesized.

TABLE 2

| Code | Sequence SEQ ID NO |
|---|---|
| -7L15 | *NTNSNSMSENVEQHN#24 |
| 1L15 | *MSENVEQHNPINAGT#25 |
| 5L16 | *VEQHNPINAFTELSAT#26 |
| 6L15 | *EQHNPINAGTELSAT#27 |
| 7L15 | *QHNPINAGTELSATG#28 |
| 8L15 | *HNPINAGTELSATGN#29 |
| 10L16 | *PINAGTELSATGNESG#30 |
| 13L15 | *AGTELSATGNESGGG#31 |
| 82L17 | IHVLNSESGSAGQMVQD#32 |
| 225L15 | *GQSQQITDSIQTGLH#33 |
| 293L20 | LTEPTTEGDQHPGTLPAANTC#34 |
| 346L15 | YSNGGPFLTPIVPTAD#35 |
| 364L15 | *YNDDEPNGAIRFTMG#36 |
| 380L19 | *QHGHLTTSSQELERYTFNP#37 |
| 408L19 | QQFNQQAPLNLENTNNGTL#38 |
| 427L18 | *LPSDPIGGKSNMHFMNTL#39 |
| 294L11/87L8 | TEPTTEGDQHPNSESGSAG#40 |

It can be seen that of the seventeen peptides synthesized eight are located at the terminal amino region of VP2 in PPV whereas the remaining nine are located at internal VP2 regions in PPV. The length of the peptides varies between 15 and 20 residues, not including the N-terminal cysteine that is used for coupling purposes. They were all sufficiently soluble to allow their conjugation to KLH.

The synthesis of these 17 peptides was carried out using Fmoc chemistry, pursuant to a general process mentioned above, on RINK™ resins, i.e. amide resins resins (Example 1). The sequences were obtained from the VP2 protein in PPV (Ranz et al., cited supra; Sakurai et al., Virus Res. 13, 79–86 (1989)). The sequences are acetylated at the N-terminal end and amidated at the C-terminal. Some peptides were purified in accordance with the protocol described in Example 1.

Example 3

CONJUGATING THE PEPTIDES TO KLH

Coupling of the purified peptides to the carrier KLH protein (Calbiochem) was carried out in accordance with standard processes using m-maleimidobenzoyl-N-succinimide ester (MBS) as coupling agent (Lerner et al. (1981) Proc. Natl. Acad. Sci. USA 78, 3403–3407). The dialysis steps were carried out at 4° C. and the other incubations at room temperature. One mg of peptide was added to every mg of KLH after attachment of a linker to the protein and this was incubated overnight at room temperature. The conjugates were then stored either directly (conjugates not dialyzed) or dialyzed, with three changes of 0.1M, pH:5.0 sodium phosphate overnight against phosphate buffered saline solution (PBS). The conjugates were divided into aliquot parts containing 1 mg of KLH and were stored at −20° C. The ratios of μg of peptide per mg of KLH varied between 82 and 304, depending upon the peptide used.

Example 4

IMMUNIZATION OF RABBITS WITH CPV PEPTIDES

New Zealand White rabbits were used for immunizations using peptides with a view to inducing neutralizing antibodies. The peptide-KLH conjugates (not dialyzed) corresponding to 1 mg of peptide in 1 ml of buffer (PBS) were mixed with an equal volume of Freund complete adjuvant (FCA) and were intramuscularly and subcutaneously injected into rabbits. After 65 days the animals received a second immunization with the same immunogen mixed with Freund incomplete adjuvant (FIA) Blood was taken on days 0, 57, 64 and 70. When the titres of anti-peptide antibodies in the peptide ELISA increased by a factor of at least 5 after the second immunization, the animals received a second boost with the same amount of conjugate in FIA on day 72 and blood was taken on days 80 and 102.

4.1 Assessment of the Anti-CPV Antibody Titre in Rabbit Serum 4.1.A. Specific virus ELISA The presence of specific anti-CPV antibodies in the serum of the immunized animals was established with an indirect ELISA assay. The antigen used was purified virus. Briefly, polystyrene plates were coated with 0.5 μg of virus in 100 μl of carbonate buffer (0.05M, pH 9.6) at 4° overnight. The plates were washed with PBS (0.15M NaCl in 0.1M sodium phosphate pH 7.4) containing 0.5% TWEEN-20™, a sorbitan derivative, namely sorbitan mono-9-octadecenoate poly (oxy-1,2-ethanediyl) derivatives, and were incubated with the antiserum for 2 h at 37° C., washed again and incubated with anti-rabbit goat IgG labelled with biotin for 1 h at room temperature. They were subsequently incubated with streptavidin labelled with peroxidase for 30 min at room temperature. The plates were washed again and the reaction was developed with o-phenylenediamine (OPD) as a substrate for peroxidase, for 10 min in darkness and read at 450 nm in a multichannel spectrophotometer.

The results obtained are shown in Table 3, from which it follows that all the rabbits produced anti-CPV antibodies.

4.1.B Specific peptide ELISA

An indirect ELISA assay was used to establish the presence of anti-peptide antibodies. Flat bottom polystyrene plates were coated overnight with 1 μg of peptide in a 50 mM sodium carbonate solution pH 9.6 at 4° C. The first antibody, rabbit serum diluted in incubation buffer comprising PBS containing 4% (v/v) of horse serum, 1% (v/v) of TWEEN-80™, a sorbitan derivative, namely sorbitan mono-9-octadecenoate poly(oxy-1,2-ethanediyl) derivatives, and NaCl 0.5M were added. After incubating for 1 h at 25° C., the plates were washed with PBS containing 0.05% (v/v) of TWEEN-80™ a sorbitan derivative. The plates were then incubated with anti-rabbit IgG-peroxidase conjugates diluted 1/100 in the incubation buffer, and the plates were washed as before. Finally, the coloured reaction was formed adding the substrate tetramethylbenzidine (Aldrich) in 0.1M sodium acetate pH 5.5 and 0.035% $H_2O_2$ (v/v) for 20 min at room temperature. The reaction was stopped adding 50 μl of 1.5M $H_2SO_4$. The absorbance was measured at 450 nm.

The results obtained are shown in Table 3 from which it follows that all the rabbits produced antibodies against the peptides used to immunize the same.

4.2. Neutralization of CPV "in vitro"

Neutralization was established with a monolayer protection test. Briefly, a known amount of CPV (100 units of HA) was incubated with rabbit antiserum at different dilutions for 2 hours at 37° C. The samples were then inoculated on monolayers of susceptible CRFK cells (ATCC CCL 94) for 90 min at 37° C. The monolayers were coated with 1 ml of 1% agarose in fresh medium. Five days after infection the cells were fixed with 10% formaldehyde in PBS for 20 min, the agarose was removed and the remaining cells were stained with 1% crystal violet in 50% ethanol for 20 min.

The level of protection was assessed by visual screening of the infected mono layers.

The results obtained are shown in Table 3 where it can be seen that the 1L15, 2L15, 3L15, 4L15, 5L15, 6L15, 7L15, 8L15 and 9L15 were capable of inducing CPV neutralizing antibodies in rabbits.

The overall results of the immunization of rabbits with CPV peptides are shown in Table 3 from which it follows that neutralization values of between 1/100 and 1/3200 were obtained. In the light of these results it can be concluded that most of the peptides located between peptides 1L15 and 7L15 induce a response of neutralizing antibodies which is even more effective than the mixture used in the vaccination of dogs. Indeed in absolute terms, the neutralization values obtained are better than the results obtained with naturally infected dog sera. This result allows it to be concluded that the twenty-five residues composing the amino terminal end of the VP2 in CPV constitute a highly immunogenic region and that peptides comprised therein contain the required antigenic potential to prepare useful synthetic vaccines to prevent canine, feline and mink parvovirosis.

TABLE 3

| PEPTIDE | ELISA | | NEUTRALIZATION TITRE |
|---|---|---|---|
| | ANTI-PEPTIDE REACTIVITY | ANTI-VIRUS REACTIVITY | |
| -10L15 | ++ | + | – |
| -5L15 | ++ | ++ | – |
| 1L15 | +++ | + | 1/100 |
| 2L15 | +++ | +++ | 1/1600 |
| 3L15 | +++ | +++ | 1/2400 |
| 4L15 | +++ | ++ | 1/200 |
| 5L15 | +++ | +++ | 1/3200 |
| 6L15 | +++ | +++ | 1/1600 |
| 7L15 | +++ | +++ | 1/500 |
| 8L15 | +++ | +++ | 1/1600 |
| 9L15 | +++ | +++ | 1/400 |
| 11L15 | + | + | – |
| 16L15 | ++** | + | – |
| 91L15 | +** | ++ | – |
| 157L17 | ++ | ± | – |
| 172L15 | ++** | ± | – |
| 283L15 | ++ | +++ | – |
| 296L15 | +** | ++ | – |
| 498L15 | +** | + | – |
| 549L15 | ±** | ++ | – |
| 570L15 | + | ++ | – |

Key to the symbols
Anti-peptide titres: +: $\leq 10^3$; ++: $10^3-10^5$; +++: $\geq 10^5$.
Anti-virus ELISA: ±: $\leq 10^2$; +: $10^2-10^3$; ++: $10^3-10^4$; +++: $\geq 10^4$.
**: Measured by PEPSCAN (elsewhere by anti-peptide ELISA) at a serum dilution of 1/100, ±: $\leq 0.300$; +: 0.3–1.0 and ++: $\geq 1.0$ absorbance units (optical density)

It can be seen that all the rabbits produced antibodies against the respective peptides used in immunization. The most outstanding result was obtained with the 1L15, 2L15, 3L15, 4L15, 5L15, 6L15, 7L15, 8L15 and 9L15 peptides which were capable of inducing neutralizing antibodies, some, 2L15, 3L15, 5L15, 6L15 and 8L15 peptides at levels similar to those obtained when using complete virus as immunogen (>1:1600). Any of these peptides or combinations thereof can be selected for inducing neutralizing antibodies in dogs and their application as a vaccine.

Example 5

DOG IMMUNIZATION

In order to verify the vaccinal effect of peptides on the natural hosts (dogs) an immunization test was made which included the subsequent infection with the same virus. The test animals used were three SPF (specific pathogen free) Beagle dogs. Two of the dogs (identified as 3029 and 3030) were immunized with a mixture in equal parts of the 1L15 and 7L15 peptides separately conjugated to KLH. The immunization mixture or cocktail (2.5 ml of total volume) contained 1 mg of each of the peptides coupled to KLH adsorbed on alumina gels and with QuilA adjuvant (25 µg/dog). The vaccination schedule was as follows: the first dose was given on day 0, and 4 weeks later they were given a record dose. Ten weeks later the virulent virus challenge test was made, lying under observation for a further 2 weeks. The dog used as negative control (identified as 3025) received a mixture of buffer (PBS)/adjuvant without conjugate. The dogs were bled on days 0, 15, 29, 36, 43, 50, 57, 64, 71 and every three days after the challenge until the test was over.

The faeces of a dog that had died as a consequence of a parvovirus infection and which contained virulent virus were used for the challenge. The faeces were homogenized in sterile culture medium and the virus was extracted with chloroform. This material was applied in oral-nasal swabs on the dogs at the time of infection. The presence of CPV in these faeces had been checked using hemagglutination and cell culture techniques. The anti-CPV antibody titre in the serum of the dogs was assessed by:

a) Specific virus ELISA

Figure 1:
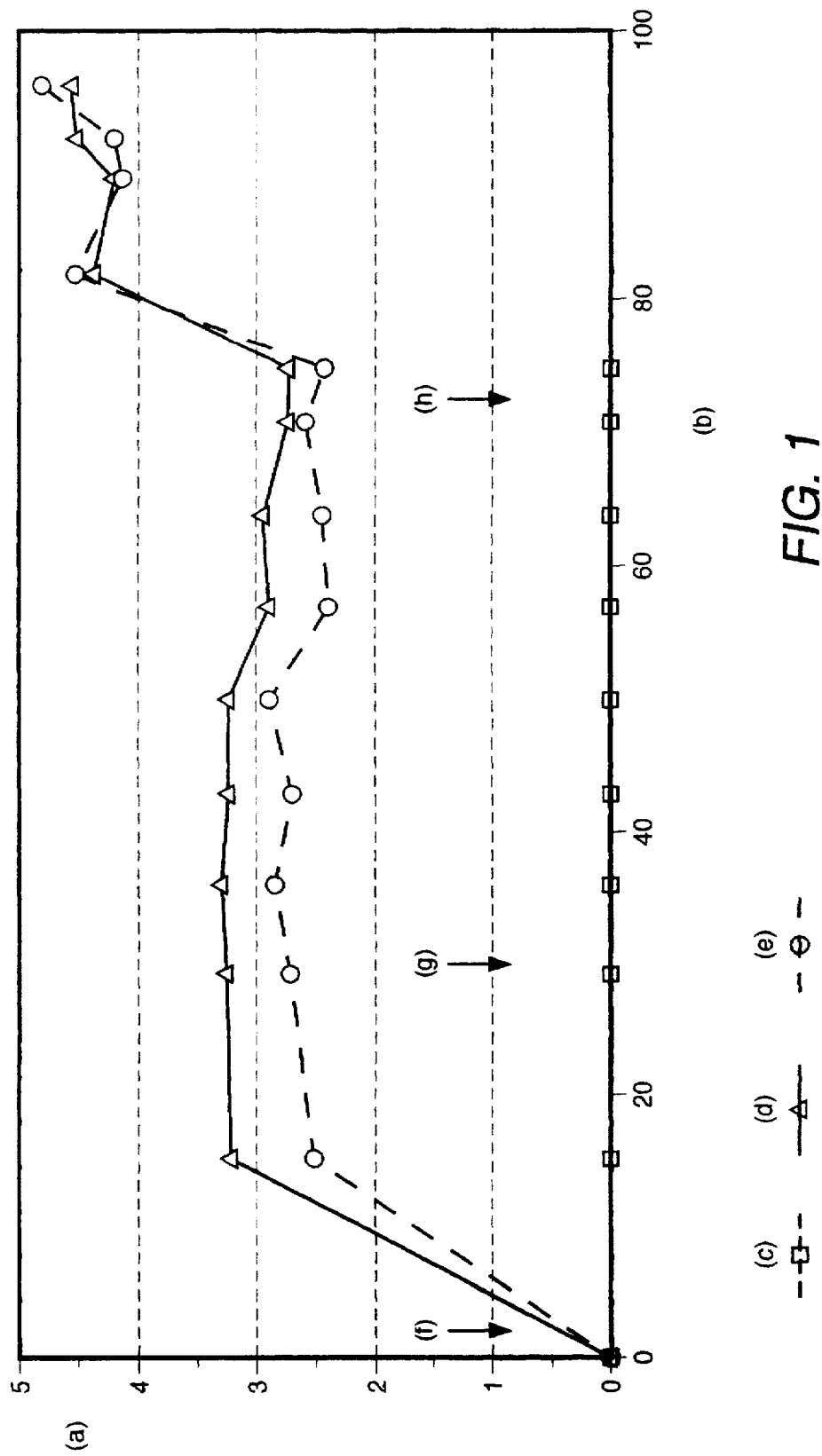
FIG. 1: shows the results obtained in establishing the titre of anti-CPV antibodies present in the serum of dogs immunized with the peptides of this invention (dogs 3029 ▲ and 3030 ⊖) and in a control dog (3025 ⊟) using a specific virus ELISA (Enzymatic Immunoassay)

The protocol described in section 4.1.A above was followed albeit using dog antisera as first antibody and incubating the plates containing such antisera with Protein A labelled with peroxidase for 1 h at room temperature. The reaction was developed with OPD and read at 450 nm in a multichannel spectrophotometer. The results obtained are shown in FIG. 1 from which it follows that after some 15 days post-1st vaccination, the immunized animal (dogs 3029 ▲ and 3030 ⊖) sera contained high anti-CPV antibodies titres, which were relatively constant after the 2nd immunization (4th week). Subsequently, after the virulent virus challenge test, there was a slight increase in the CPV antibody titre in the immunized dogs, and the control dog (dog 3025 ⊟) died after 6 days.

b) Specific peptide ELISA

The protocol described in example 4.1.B was followed though serum was added to the dogs to be assessed diluted in the incubation buffer as first antibody. The plates were subsequently incubated with anti-dog IgG-peroxidase conjugates diluted 1/100 in the incubation buffer and finally the coloured reaction was formed adding tetramethylbenzidine, stopped with $H_2SO_4$ and absorbance was measured at 450 nm.

Figure 2:
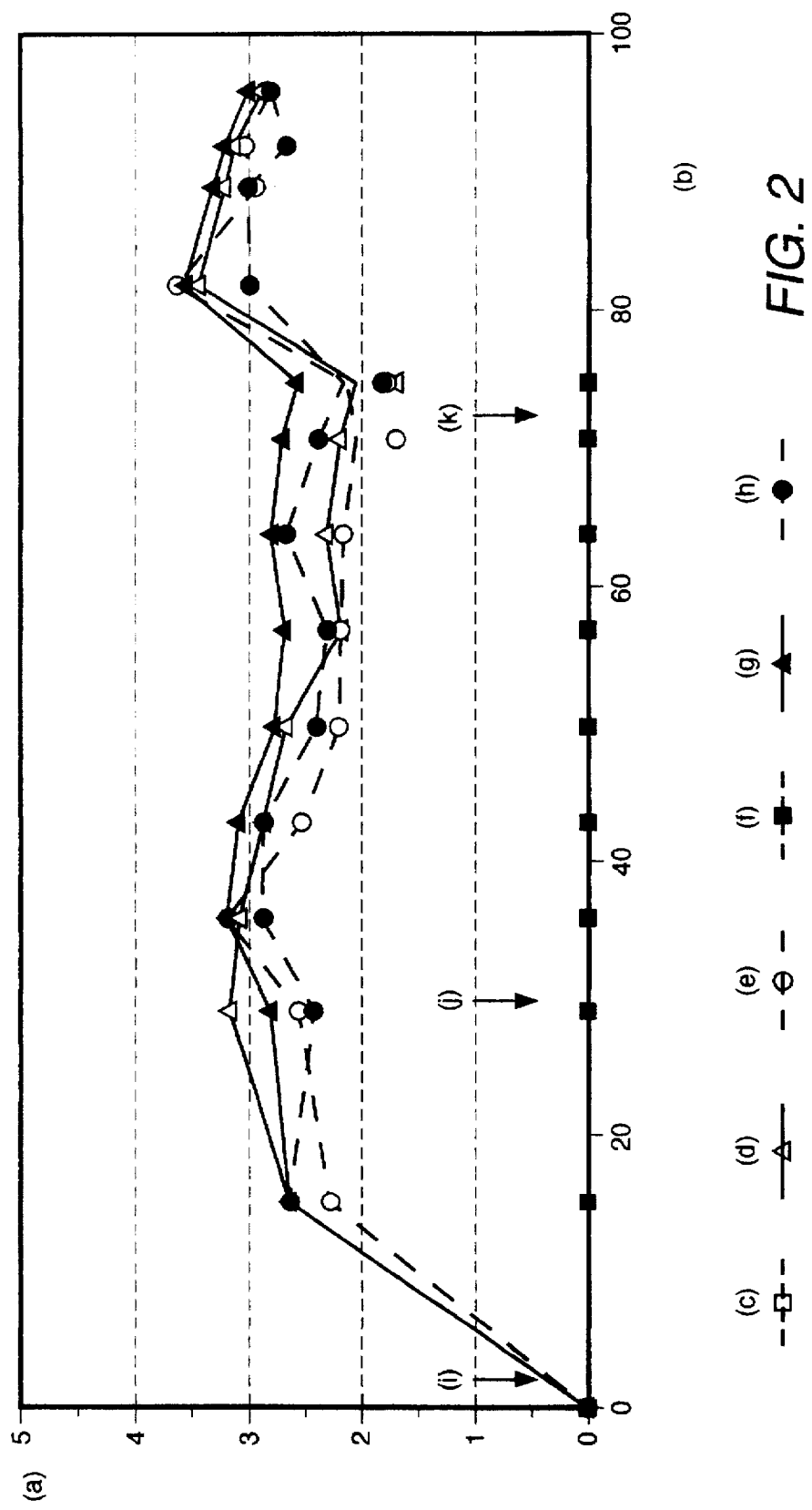
FIG. 2: shows the results obtained in establishing the titre of anti-peptide antibodies (1L15 and 7L15) present in the serum of immunized dogs (3029 and 3030) and in the sentry dog (3025), using a specific peptide ELISA, according to the following key.

The results obtained are shown in FIG. 2 from which it follows that the immunized dogs (3029 and 3030) produced antibodies which recognized the 1L15 [(3029 ▲) and (3030 ⊖)] and 7L15 [(3029 ▲) and (3030 ●)] peptides whereas the serum of the negative control dog (3025) contained no antibodies recognizing the 1L15 (⊟) and 7L15 (■) peptides. After the virulent virus challenge the control dog (3025) died whereas the sera of the immunized dogs increased slightly in their antibody content recognizing the 1L15 and 7L15 peptides.

c) "In vitro" neutralization of CPV

The protocol described in Example 4.2 was followed but the CPV was incubated with antiserum of the dogs (3025, 3029 and 3030) at different dilutions. After inoculating the samples on monolayers of CRFK cells and continuing the aforesaid protocol the results shown in FIG. 3 were obtained, from which it follows that the immunized dogs (3029 ▲ and 3030 ⊖) produced neutralizing antibodies at levels similar to those obtained using complete virus as immunogen (approximately 1:1000). The control dog (3025 ⊟) however never produced any neutralizing antibodies before the challenge.

d) Establishing CPV in dog faeces

The presence of CPV in immunized dog faeces was established using a double antibody sandwich ELISA assay (ELISA-DAS) pursuant to the methodology described by Rimmelzwaan et al. (Vet. Quart., 1990, 12, 14–20). The results obtained are shown in FIG. 4 from which it follows that the faeces of the immunized dogs (3029 ▲ and 3030 ⊖) contained almost no CPV whereas the faeces of the control dog (3025 ⊟) however contained high CPV levels after the virulent virus challenge.

e) Clinical assessment

Together with the previously described serological data the progress of the disease was clinically monitored, recording temperature and external signs daily. The animal faeces were also collected daily. Clinically, it was found that the animals immunized with the 1L15 and 7L15 peptides (dogs 3029 and 3030) never showed any virtual symptoms of the disease, whereas the control dog (3025) died after 6 days, showing all characteristic symptoms of parvovirosis (diarrhoea, blood in stools and presence of CPV). The two immunized dogs developed high anti-peptide and anti-CPV antibody titres, including a high neutralizing activity which reached its peak on week 5 (FIG. 3) after the 1st immunization. The second dose did not reinforce the antibody titre. The control dog was negative over the first vaccination period. After the oral-nasal challenge with CPV, both vaccinated dogs were healthy for the complete period.

Example 6

MINK IMMUNIZATION

This mink immunization test was made due to the close homology between CPV, FPLV and MEV in order to experimentally check the effectiveness of these new peptides in the design of MEV vaccines.

6.a Immunization

Three groups of minks (genotype A/A, seronegative for the Aleutian disease virus and the mink enteritis virus (MEV)) were used. Group 1 (nos. 1–6) were vaccinated with 0.5 mg of the 1L15 peptide coupled to 0.5 mg of KLH plus 0.5 mg of the 7L15 peptide coupled to 0.5 mg of KLH, using 50 μg of ISCOM matrix as adjuvant, all in a final volume of 1 ml of PBS (pH: 7.2). Group 2 (nos. 7–12) only received 1 ml of PBS (pH: 7.2). Group 3 (nos. 13.18) received a conventional vaccine (BIOVAC™, United, DK) based upon inactivated virus which was administered following the manufacturer's recommendations. The minks all received a single subcutaneous vaccinal dose and were bled just before vaccination.

6.b Challenge

Blood samples were taken twenty-one days after vaccination and the minks were left fasting for 24 h. They were then infected by oral-nasal means using 0.8 ml of a 25% intestinal homogenate of minks suffering from acute MEV infection. Fecal samples of all the minks were checked daily to detect MEV, using an ELISA based upon specific rabbit antisera. The animals in group 2 (negative controls) secreted massive amounts of virus on days 5, 6 and 7 after the challenge. They were all sacrificed without pain in dying state because of a severe disease.

The two other groups of minks secreted no virus in their faeces. Only one mink in group 1 displayed a small indication of virus on day 6, though all the animals were clinically normal, free from diarrhoea and had a good appetite throughout the test.

The virus secreted by the control group was extracted from the positive fecal samples and underwent immunoelectron microscopy, and the presence of a large number of MEV particles was confirmed.

6.c Establishing neutralizing antibodies

The sera of the minks were all checked for their neutralizing activity on MEV cultivated in CRFK cells. The non-neutralized virus was detected by means of the immunoperoxidase technique using microtitre plates containing CRFK cells infected with 100 $DICT_{50}$ (50% tissue culture infective dose) of MEV, infected for 4 days and fixed (M. Holm-Jensen, Acta Vet. Scand., 22:85–98 (1981)). Incubation at 37° C. for 1 h with an an linked to peroxidase and development followed. The titres obtained are shown in Table 4. The titre at the final point was stated as the highest inverse serum dilution neutralizing the virus infection on the monolayer of cells.

Twenty-one days after vaccination the groups that had received the commercial vaccine showed good neutralization titres (>3log10). The control animals and the group vaccinated with the peptidic vaccine showed no neutralizing antibodies in the "in vitro" assay, which indicates that complete disease protection can be obtained induced by a synthetic peptide without inducing neutralizing antibodies "in vitro". It could be speculated that protection could be due to either the inhibition of a cell attachment site by the antibodies to the peptide or the induction of a mechanism mediated by cells.

Two weeks after the challenge the minks all showed MEV neutralizing antibodies. In conclusion, it can be stated that with a synthetic vaccine based upon the peptides of this invention solid protection of minks can be obtained, and they can hence also be formulated in the preparation of an effective vaccine.

TABLE 4

| Mink | Titre (log10) [21 days post-vaccination] | Titre (log10) [14 days post-challenge] |
|---|---|---|
| 1 | <1.0 | 2.7 |
| 2 | <1.0 | 3.1 |
| 3 | <1.0 | 3.0 |
| 4 | <1.0 | >3.1 |
| 5 | <1.0 | >3.1 |
| 6 | <1.0 | 3.1 |
| 7 | <1.0 | 3.1 |
| 8 | <1.0 | >3.1 |
| 9 | <1.0 | >3.1 |
| 10 | <1.0 | >3.1 |
| 11 | <1.0 | >3.1 |
| 12 | <1.0 | 3.0 |
| 13 | >3.1 | >3.1 |
| 14 | >3.1 | >3.1 |
| 15 | >3.1 | >3.1 |
| 16 | >3.1 | >3.1 |
| 17 | >3.1 | >3.1 |
| 18 | >3.1 | >3.1 |

Example 7

RABBIT IMMUNIZATION WITH PPV PEPTIDES

New Zealand White rabbits were used for immunizations with peptides with a view to inducing neutralizing antibodies. The peptide-KLH conjugates corresponding to 1 mg of peptide in 1 ml of buffer (PBS) were mixed with an equal volume of Freund complete adjuvant (FCA) and intramuscularly and subcutaneously injected into rabbits. After 42 days the animals received a second immunization with the same immunogen mixed with Freund incomplete adjuvant (FIA). Blood was taken on days 0, 39, 50 and 71.

7.1 Western Blot (immunoblot)

To establish the specificity of the antibodies induced by the peptides in the rabbits a Western Blot assay was used. To this end, complete purified PPV was run in a 10% polyacrylamide-SDS (sodium dodecylsulphate) gel under the usual conditions (Laemli, U.K., Nature 227:680–685 (1970)). The proteins were then transferred to PVDF filters (polyvinylydene difluoride) (Millipore, USA) using a semi-dry apparatus (KEM-En-Tec, DK) and immunoblot was carried out pursuant to set techniques (Burnette, W. N., Anal. Biochem., 112:195–203 (1981); De Blas D. L. et al., Anal. Biochem., 133:214–219 (1983)). Briefly, the filters were blocked in a solution containing 2% skim milk for 30 minutes. Anti-PPV rabbit serum, 1:1000 diluted, was then added for 2 h at room temperature and overnight at 5° C. This was then washed twice and finally incubated for 2 h with rabbit anti-IgG labelled with peroxidase (Dako P217, DK) 1:500 diluted. The chromogen used was o-dianisidine. The results showing reactivity with the structural proteins are shown in Table 5.

7.2 Neutralization of PPV "in vitro"

Serial double dilutions of each serum, inactivated at 56° C. for 30 min, were prepared in Eagle's minimum essential medium (Eagle's MEM). Fifty µl of each dilution were then mixed with 100–300 DICT$_{50}$ of the PPV Danish strain 893 (SVIV, Lindholm) in 50 µl of Eagle medium and left to incubate for 60 min at 37° C. Each dilution was then mixed in a plate of 96 wells with 2000 primary pig kidney cells in 50 ml of Eagle's MEM and calf fetal serum up to a final concentration of 7% and was left to incubate for 4–5 days at 37° C.

The plates were stained using a monolayer immunoperoxidase assay, using a porcine anti-PPV serum, anti pig rabbit immunoglobin attached to peroxidase and blotting with amino-ethyl-carbazole, following conventional protocols (Holm-Jensen cited supra). The final point titre was stated as the highest inverse serum dilution neutralizing the virus infection on the mono layer of cells.

The results obtained are shown in Table 5 from which it follows that the 1L15, 5L16, 6L15, 8L15, 10L16 and 13L15 peptides were capable of inducing antibodies neutralizing PPV in rabbits.

TABLE 5

| PEPTIDE ANTISERA | WESTERN BLOT | NEUTRALIZATION |
|---|---|---|
| -7L15 | — | − |
| 1L15 | VP1, VP2 | + |
| 5L16 | VP1, VP2 | + |
| 6L15 | VP1, VP2 | + |
| 7L15 | — | − |
| 8L15 | VP1, VP2 | + |
| 10L16 | VP1, VP2 | + |
| 13L15 | VP1, VP2, VP3 | + |
| 83L15 | VP1, VP2, VP3 | − |
| 225L15 | VP1, VP2, VP3 | − |
| 293L20 | VP1, VP2, VP3 | − |
| 346L16 | VP1, VP2, VP3 | − |
| 364L15 | VP1, VP2, VP3 | − |
| 380L19 | VP1, VP2, VP3 | − |
| 408L19 | VP1, VP2, VP3 | − |
| 427L18 | VP1, VP2, VP3 | − |
| 294L11/87L8 | VP1, VP2, VP3 | − |

Key to the symbols:
Neutralization titre: −: <2; +: 2–20.

It is clear that all the rabbits produced antibodies against the PPV capsid proteins, which was established by Western Blot. The most outstanding result was obtained with the 1L15, 5L16, 6L15, 8L15, 10L16 and 13L15 peptides which were capable of inducing antibodies capable of neutralizing PPV "in vitro". These peptides were selected for inducing neutralizing antibodies in pigs and the application thereof as a vaccine.

Example 8

PIG IMMUNIZATION

To check the immunogenicity of peptides on the host animal the peptide designated 5L16 (Table 2) was used. Three PPV seronegative Göttingen mini-pigs were vaccinated with 1 mg of 5L16 peptide coupled to 1 mg of KLH each. The adjuvant used was ISCOM Matrix (500 µg) and the sample was taken to 2 ml with PBS. The pigs were vaccinated twice with an interval of three weeks. The serum samples were taken on days 0, 25 and 36.

8.a PPV ELISA Assay

PPV virions were adsorbed to flat bottom polystyrene plates (Nunc). Seriated dilutions (2 factor) of the pig serum were then added to the plates and incubated at 37° C. for 1 h. The plates were washed and pig anti rabbit-IgG serum conjugated to peroxidase was added. Incubation for 30 min at 37° C. and OPD blotting followed.

The three mini-pigs failed to show an anti-PPV antibodies titre on days 0 and 25. Now then, on day 36 (10 days after revaccination) significant albeit low (Table 6) titres had developed, showing that the peptidic vaccine is capable of inducing antibodies in pigs which recognize the epitope in purified PPV virions.

TABLE 6

| Mini-pig no. | Day 0 titre | Day 25 titre | Day 36 titre |
|---|---|---|---|
| 284 | 28 | 35 | 130 |
| 283 | 21 | 43 | 226 |
| 280 | 28 | 31 | 1194 |

8.b Western Blot Analysis

A Western Blot analysis was made to analyze reactivity and specificity, against the various protometers of the virus, of the sera originating in the three immunized mini-pigs.

The procedure followed to check reactivity by Western Blot was similar to that used in Example 7.1, with slight modifications. The blocking buffer contained 1% casein instead of fetal calf serum and albumin. The conjugate used was pig anti-IgG rabbit serum labelled with peroxidase (Dako P164).

The results showed a very strong reaction against VP1 and VP2 after the two immunizations. These results confirm the high immunogenicity of these peptides, which confirms that they are useful in formulating new PPV subunit vaccines.

Example 9

FORMULATING A VACCINE

Vaccines capable of protecting dogs, cats, minks and pigs respectively from CPV, FPLV, MEV and PPV infection containing one or more of the corresponding peptides provided by this invention coupled to a carrier protein or multimeric structure, or in the form of an immunogenic complex, or in the form of a recombinant immunogenic protein, with an immunologically acceptable diluent such as a physiological pH buffered saline solution, plus an adjuvant such as Alhydrogel in combination with QuilA (25 µg/animal) can be prepared. A single injection can be sufficient to confer animals with protection from the disease though, in some cases, depending upon the assessment of the antibody titre, it could be useful to use a second booster dose.

Translation of the Keys to the Figures

FIGS. 1 and 3

(a) titre logarithm
(b) days
(c) control dog (3025)
(d) vaccinated dog (3029)
(e) vaccinated dog (3030)
(f) 1st immunization
(g) 2nd immunization
(h) virulent virus challenge

FIG. 2

(a) titre logarithm
(b) days
(c) dog 3025, peptide 1L15
(d) dog 3029, peptide 1L15
(e) dog 3030, peptide 1L15
(f) dog 3025, peptide 7L15
(g) dog 3029, peptide 7L15
(h) dog 3030, peptide 7L15
(i) 1st immunization
(j) 2nd immunization
(k) virulent virus challenge

FIG. 4

(a) Absorbance×1000 (450 nm)
(b) days
(c) control dog (3025)
(d) vaccinated dog (3029)
(e) vaccinated dog (3030)
(f) 1st immunization
(g) 2nd immunization
(h) virulent virus challenge

We claim:

1. A vaccine to protect dogs from infection caused by canine parvovirus comprising:

an immunizing quantity of a peptide selected from the group consisting of: SEQ ID NO: 1; SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and SEQ ID NO: 13; and a diluent and an adjuvant, being immunologically acceptable.

2. The vaccine of claim 1, said peptide being coupled to a carrier protein.

3. The vaccine of claim 1, said peptide being coupled to a multimeric structure.

4. A vaccine to protect cats from infection caused by feline panleukopenia virus comprising:

an immunizing amount of a peptide selected from the group consisting of: SEQ ID NO: 1; SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and SEQ ID NO: 13; and a diluent and an adjuvent, being immunologically acceptable.

5. The vaccine of claim 4, said peptide being coupled to a carrier protein.

6. The vaccine of claim 4, said peptide being coupled to a multimeric structure.

7. A vaccine to protect minks from infection caused by mink enteritis virus comprising:

an immunizing amount of a peptide selected from the group consisting of: SEQ ID NO: 1, SEQ ID NO: 5 and SEQ ID NO: 11; and a diluent and an adjuvent, being immunologically acceptable.

8. The vaccine of claim 7, said peptide being coupled to a carrier protein.

9. The vaccine of claim 7, said peptide being coupled to a multimeric structure.

10. A vaccine to protect pigs from infection caused by porcine parvovirus comprising:

an immunizing amount of a peptide selected from the group consisting of: SEQ ID NO: 2, SEQ ID NO: 25, SEQ ID NO: 26, SEQ ID NO: 27, SEQ ID NO: 29, SEQ ID NO: 30, and SEQ ID NO: 31; and a diluent and an adjuvent, being immunologically acceptable.

11. The vaccine of claim 10, said peptide being coupled to a carrier protein.

12. The vaccine of claim 10, said peptide being coupled to a multimeric structure.

* * * * *